United States Patent [19]

Runge

[11] Patent Number: 4,582,644
[45] Date of Patent: Apr. 15, 1986

[54] EPI-ETHYNYLATION PROCESS

[75] Inventor: Jean R. Runge, Scotts, Mich.

[73] Assignee: The Upjohn Company, Kalamazoo, Mich.

[21] Appl. No.: 673,961

[22] Filed: Nov. 21, 1984

[51] Int. Cl.$^4$ ............................................... C07J 1/00
[52] U.S. Cl. .......................... 260/397.4; 260/397.45; 260/397.5; 260/397.3
[58] Field of Search ...................................... 260/397.4

[56] References Cited

U.S. PATENT DOCUMENTS 3,983,112  9/1976  Kanojia ........................... 260/239.55
4,022,892  5/1977  Kanojia ............................... 424/238
4,440,689  4/1984  Nitta ................................... 260/397.4
4,443,377  4/1984  Van Rheenen ................... 260/397.4

FOREIGN PATENT DOCUMENTS 53845  6/1982  European Pat. Off. .

OTHER PUBLICATIONS

Journal of Organic Chemistry, 39, 2304–2306 (1974), R. M. Kanojia, et al., "Epimerization of Mestranol Acetate on Alumina".
Journal of Medicinal Chemistry, 22, No. 12, 1538–1541 (1979), R. M. Kanojia, "Synthesis and Estrogenic Properties of 17-Epi-Ethynylestradiol and Its ... ".
Tetrahedron Letters, 21, 2665–2666 (1980), H. Westmijze et al., "Ag(I)-Assisted Hydrolysis of Mestranol Methanesulfonate into Epimestranol".
Chem. Ber III, 3086–3093 (1978) H. Hofmeister et al.

Primary Examiner—Elbert L. Roberts
Attorney, Agent, or Firm—Bruce Stein

[57] ABSTRACT

Ethynylation of 17-keto steroids (I) by standard means in the presence of a polar amine solvent produces the epi (17$\beta$-ethynyl-17$\alpha$-hydroxy) configuration at $C_{17}$. The epi-ethisterone compounds are useful intermediates in the production of 17$\alpha$-hydroxyprogesterones.

28 Claims, No Drawings

EPI-ETHYNYLATION PROCESS

BACKGROUND OF THE INVENTION

Ethynylation of 17-keto steroids (I) to produce the ethisterone type steroids (III) where the stereochemistry at $C_{17}$ is 17α-ethynyl-17α-hydroxy is well known to those skilled in the art. Epiethisterone type compounds (II) have the 17β-ethynyl-17α-hydroxy configuration at $C_{17}$.

While the 17α-ethynyl-17β-hydroxy or regular configuration is by far most common, the epi-configuration (17β-ethynyl-17α-hydroxy) is known. Kanojia et al. in J. Org. Chem. 39, 2304 (1974) reported the epimerization of mestranol on an alumina column to epimestranol in 5% yield.

Kanojia et al. in J. Med. Chem. 22, 1538 (1979) reported ethynylating estrone 3-methyl ether with acetylene, potassium hydroxide in N-methylpyrrolidinone and obtained the corresponding expected 17α-ethynyl-17β-hydroxy product (mestranol) in 87% yield and also obtained the epimeric 17β-ethynyl-17α-hydroxy epimestranol in 13% yield by quantitative TLC. After column chromatography the epimestranol was obtained in 7% yield.

Kanojia in U.S. Pat. Nos. 3,983,112 and 4,022,892 discloses the epimerization of 17-acyl esters 17α-ethynyl-3,17β-estradiol 3-ethers to 17β-ethynyl-3,17α-estradiol by activated alumina.

Others have reported the $C_{17}$ epimerization of the propargyl alcohol using heavy metals. For example, silver has been reported in the $C_{17}$ isomerization by Westmizze et al. in Tetrahedron Letters 21, 2665 (1980), in European Pat. No. 53,845 and by Hofmeister et al. in Chem. Ber. 111, 3086 (1978).

European Pat. No. 53,845 and U.S. Pat. No. 4,440,689 also reported the isomerization of certain nitric and sulfonic acid esters with copper salts.

The process of the present invention is an epimerization process and produces the epi-configuration of ethisterone directly in greater than 25% chemical yield.

SUMMARY OF THE INVENTION

Disclosed is a process for the preparation of a 17β-ethynyl-17α-hydroxy steroid (II) in greater than 25% chemical yield which comprises (1) contacting a 17-keto steroid (I) with an acetylene source in the presence of a strong base with an epi-amine solvent selected from the group consisting of ethylenediamine, 1,3-propylenediamine, 1,2-diaminopropane, triethylenetetramine, 1,2-d-iaminocyclohexane, constituting at least 5% of the reaction medium and (2) quenching the reaction mixture with a quenching agent.

Further disclosed is a process for the preparation of a 17β-ethynyl-17α-hydroxy steroid (II) which comprises (1) contacting a 17α-ethynyl-17β-hydroxy steroid (III) with a strong base in an epi-amine solvent selected from the group consisting of ethylenediamine, 1,3-propylenediamine, 1,2-diaminopropane, triethylenetetramine and 1,2-diaminocyclohexane constituting at least 5% of the reaction medium.

DETAILED DESCRIPTION OF THE INVENTION

The 17-keto steroid (I) starting materials are well known to those skilled in the art or can be readily prepared from known compounds by methods well known to those skilled in the art. Further, these steroids are known in the $C_3$ protected forms, for example, the enol ether (U.S. Pat. No. 3,516,991) and the 3-enamine (U.S. Pat. No. 4,216,159).

The 17-keto steroid (IA–IC) starting materials may have variable substituents at positions 1, 6, 9, 10 and 11, as is well known to those skilled in the art. It is preferred in the $\Delta^4$-3-keto series (A) that $R_6$ be a hydrogen atom, methyl or methylene group but in the $\Delta^{1,4}$-3-keto series (B) that $R_6$ be a hydrogen or fluorine atom.

The 17-keto steroids (IA–IC) may or may not have to have the functionality at $C_3$ protected during the ethynylation process of this invention depending on the nature of the steroid A ring (A–C), see Chart B. For the $\Delta^4$-3-keto steroid (A) the $C_3$ ketone is preferably protected as the enol ether (Aa), ketal (Ab), or enamine (Ac) as is well known in the art, see Chart C. The preferred enol ether (Aa) is the methyl or ethyl ether. The preferred ketal (Ab) is the ethylene ketal. The preferred enamines are selected from the group consisting of pyrrolidine, morpholine and diethylamino amines. The enol ethers (a) are prepared by methods well known in the art, see J. Org. Chem. 26, 3925 (1961), Steroid Reactions, Edited by Carl Djerassi, Holden-Day, San Francisco 1963, page 42–45, and U.S. Pat. No. 3,516,991 (Preparation 1). The ketals (b) are also prepared by well known methods, see Steroid Reactions, supra, page 11–14. The 3-enamines (c) are also prepared by methods well known in the art, see U.S. Pat. Nos. 3,629,298 and 4,216,159 and Steroid Reactions, supra, page 49–53.

The $\Delta^{1,4}$-3-keto steroids (B) do not have to have the $C_3$ ketone protected.

The 3-hydroxy steroid (C) may have the 3β-hydroxyl group protected as the ether (Ca), see Chart C. The preferred blocking groups are methyl, ethyl, ethoxy ethyl (EEE), tetrahydropyranyl (THP) and trimethylsilyl (TMS).

The ethynylation reaction of the present invention is performed as the ethynylation reaction of any 16-unsubstituted-17-keto steroid (I) as is well known to those skilled in the art, with the exception that the reaction medium must contain at least 5% of an epi-amine solvent. An epi-amine solvent is an amine which if used as the solvent or co-solvent in an ethynylation reaction of a 17-keto steroid (I) changes the ratio of 17α-ethynyl-17β-hydroxy/17β-ethynyl-17α-hydroxy from greater than 90/10 to less than 75/25. The reaction requires an acetylene source which can be acetylene, calcium carbide, or potassium carbide or any other reagent which generates acetylene in situ. The preferred acetylene source is selected from the group consisting of potassium carbide.

The reaction also requires a strong base such as t-butoxide, i-propoxide, methoxide, ethoxide, or —OR where R is alkyl of 1 thru 5 carbon atoms. Equivalent to a strong base such as potassium t-butoxide are reagents which generate the strong base in situ such as potassium hydroxide and t-butanol. It is preferred that the strong base be t-butoxide or hydroxide and t-butanol.

It is preferred that the counterion be potassium. Other cations such as sodium are operable but the reaction time greatly increases.

Ethynylation reactions are conveniently performed in ether solvents such as THF, ether, dioxane or the equivalent. If performed in an ether solvent in the absence of epi-amine, the product has the 17α-ethynyl-17β-hydroxy configuration at $C_{17}$. If the reaction is permitted to run for extended periods of time (2–4 days), then some ethynylated product with 17β-ethynyl-17α-hydroxy (epi) steriochemistry at $C_{17}$ is detected, but the ratio of 17α-ethynyl to 17β-ethynyl is still small and time dependent. It has been surprisingly and unexpectedly found that if the ethynylation reaction is performed under normal conditions but in the presence of at least 5% of an epi-amine solvent, at least 25% of the epi isomer is found and usually about 50% of the epi isomer is obtained. It is most preferable that the reaction solvent be 100% epi-amine, at least 50% epi-amine is preferred while 5% is operable. Operable epi-amines include, for example, ethylenediamine, 1,3-propylenediamine, 1,2-diaminopropane, triethylenetetramine, 1,2-diaminocyclohexane, and equivalents thereof. Preferred is ethylenediamine, 1,3-propylenediamine, 1,2-diaminopropane, and triethylenetetramine or most preferred is ethylenediamine. The reaction is performed at 20° or greater.

When the reaction is complete as measured by TLC, it is quenched as is well known to those skilled in the art. Operable quenching agents include acetic acid, water, saline, and aqueous buffer.

Following quenching the reaction mixture is worked up as is well known to those skilled in the art to obtain the $C_{17}$-epi 17β-ethynyl-17α-hydroxy steroid (II). If there is a mixture of $C_{17}$ epimers the mixture is separated by chromatography or by selective crystallization from toluene, isopropanol or ethyl acetate.

The 17β-ethynyl-17α-hydroxy steroids (II) are useful because they can be readily transformed to the corresponding 17α-hydroxyprogesterone by reaction with a mercuric agent. Oxymercuration of ethisterone derivatives is well known, see Helv. Chim. Acta 26, 680 (1943) and U.S. Pat. No. 4,443,377.

Following the oxymercuration reaction, any mercury contamination should be aleviated. It does not have to be removed immediately but can be removed during another step in the synthesis. The mercury is preferably removed by the use of zinc dust and acetic acid, which is the invention of another.

The mercuric agent can be produced by reaction of mercuric oxide with a strong acid such as sulfuric, hydrochloric, or nitric acid. The mercuric salts, mercuric sulfate, mercuric chloride or mercuric nitrate can be used directly in acid medium. Mercuric sulfate or this salt made from mercuric oxide and sulfuric acid is preferred. A catalytic amount of a mercuric agent and the 17β-ethynyl-17α-hydroxy steroid (II) are contacted at 20°–65° for 2–24 hr in an aqueous polar solvent. When the oxymercuration reaction is complete, the reaction mixture is filtered (thru celite) to remove insoluble mercuric salt solids and the 17α-hydroxy progesterone is recovered from the filtrate by means well known to those skilled in the art. Alternatively the oxymercuration reaction can be performed using the mercuric agent affixed to a resin. See M. S. Newman, J. Am. Chem. Soc., 75, 4740 (1953).

DEFINITIONS

The definitions and explanations below are for the terms as used throughout the entire patent application including both the specification and the claims.

All temperatures are in degrees Centigrade.

TLC refers to thin-layer chromatography.

THF refers to tetrahydrofuran.

THP refers to tetrahydropyranyl.

EEE refers to ethoxy ethyl ether [—O—CH(CH$_3$)OCH$_2$CH$_3$].

TEA refers to triethylamine.

Saline refers to an aqueous saturated sodium chloride solution.

NMR refers to nuclear (proton) magnetic resonance spectroscopy, chemical shifts are reported in ppm (δ) downfield from tetramethylsilane.

TMS refers to trimethylsilyl.

When solvent pairs are used, the ratios of solvents used are volume/volume (v/v).

Androstenedione refers to androst-4-ene-3,17-dione.

R is alkyl of 1 thru 5 carbon atoms.

$R_3$ is alkyl of 1 thru 5 carbon atoms with the proviso that with the ketal (Ab), and the enamine (Ac), the $R_3$ groups can be the same or different and can be connected.

$R_3'$ is alkyl of 1 thru 3 carbon atoms, a TMS, THP or EEE group.

$R_6$ is a hydrogen or fluorine atom or methyl or methylene group.

$R_9$ is nothing, a hydrogen, fluorine or oxygen atom which makes the C ring
  (a) $\Delta^{9(11)}$ when $R_9$ is nothing and
  (b) 9β,11β-epoxide when $R_9$ is an oxygen atom.

$R_{11}$ is a hydrogen or oxygen atom, two hydrogen atoms, or α- or β-hydroxyl group which makes the C-ring
  (a) $\Delta^{9(11)}$ when $R_{11}$ is a hydrogen atom,
  (b) 9β,11β-epoxide when $R_{11}$ is an oxgen atom and . . . between $C_{11}$ and $R_{11}$ is a single bond, and
  (c) a ketone when $R_{11}$ is an oxygen atom and . . . . between $C_{11}$ and $R_{11}$ is a double bond.

$R_{19}$ is a hydrogen atom or methyl group.

~ indicates that the attached group can be in either the α or β configuration.

. . . . is a single or double bond.

When the term "alkyl of ___ through ___ carbon atoms" is used, it means and includes isomers thereof where such exist.

An epi-amine solvent is an amine which if used as the solvent or co-solvent, in at least 5% (v/v), in an ethynylation reaction of a 17-keto steroid (I) accelerates the formation of $C_{17}$ epimeric compounds 17α-ethynyl-17β-hydroxy-/17β-ethynyl-17α-hydroxy from a ratio greater than 90/10 to a ratio less than 75/25 and gives a yield of at least 25% epi.

Ether refers to diethyl ether.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

17β-Ethynyl-17α-hydroxy-3-methoxyandrosta-3,5-diene (IIAa)

Potassium hydroxide pellets are pulverized in a commercial blender to a fine powder.

Calcium carbide "lumps" of 38% purity varying in size from about 0.25 to about 1.5" in diameter are pulverized in a commercial blender and then filtered thru a 20 mesh wire screen.

Potassium hydroxide (7.75 g), calcium carbide (21.0 g), t-butanol (19 ml) and ethylene diamine (187 ml) are combined in a 500 ml Parr pressure bottle which is sealed with a foil covered rubber stopper which is wired to the bottle. The heterogenous mixture is stirred at 40° for about 16 hr (though about 4 hr is sufficient). The mixture is cooled to 20°–25° and 3-methoxyandrosta-3,5-dien-17-one (IAa, 11.80 g) is added as a solid. The reaction mixture is then stirred at 20°–25° for 5 hr. The mixture is transferred to a flask with a mechanical stirrer. The mixture is washed with methylene chloride (300 ml), cooled to 0°, quenched under a nitrogen atmosphere by the slow addition of acetic acid (57.2 ml). Water (300 ml) is added at a sufficiently slow rate to keep foaming under control. The mixture is filtered and the solids washed with methylene chloride. The filtrate phases are separated, the aqueous phase is back-extracted (twice) with methylene chloride. The organic phases are combined, washed with water (three times), dried over sodium sulfate and concentrated to an oil. The oil in ethyl acetate (75 ml) is heated to reflux and is allowed to crystallize at 20°–25° overnight to give the title compound, NMR (CDCl$_3$) 0.90, 1.0, 2.47, 3.59, 5.15 and 5.23 δ.

EXAMPLE 2

17β-Ethynyl-17α-hydroxyandrosta-4,9(11)-dien-3-one (II A)

17α-Ethynyl-17β-hydroxyandrosta-4,9(11)-dien-3-one (III A, (.S. Pat. No. 3,441,559, 0.3 g) and potassium t-butoxide (0.119 g) are combined in a vial which is then sealed with a septum and aluminum cap. The vial air-space is evacuated under reduced pressure, ethylene diamine (5 ml) is then added by a syringe followed by acetylene gas purge into the vapor space. The mixture is stirred at 20°–25° for 48 hours at which time TLC (ethyl acetate/hexane:50/50) indicates the title compound is obtained.

EXAMPLE 3

17β-Ethynyl-17α-hydroxy-3-methoxyandrosta-3,5-diene (IIAa)

In an inert pressurizable vessel is placed 3-methoxyandrosta-3,5-dien-17-one (I Aa, 15 g) THF (60 ml), milled potassium hydroxide (15 g), t-butanol (1.5 ml), and ethylenediamine (10 ml). The stirred mixture is heated to 53° and a 15-pound partial pressure of acetylene is applied. These conditions are maintained for 3 hr at which time TLC indicates a mixture of ethisterone methyl enol ether and epiethisterone methyl enol ether. The reaction mixture is quenched with phosphate buffer (pH=7) and methylene chloride is used to isolate the product as an oil. The resulting oil is crystallized from toluene to give epi-ethisterone enol ether of approximately 90% purity.

EXAMPLE 4

17α-Hydroxypregna-4,9(11)-diene-3,20-dione

Mercuric oxide red (0.064 g) and concentrated sulfuric acid (0.086 ml) are stirred in water (1 ml) for 75 minutes at 67°. This mercuric oxide mixture is added to a mixture of 17β-ethynyl-17α-hydroxyandrosta-4,9(11)-dien-3-one (II A, Example 2, 0.84 g) in THF (5 ml) and methanol (24 ml) at 38°. This mixture is stirred for 3 hours and then cooled to 20°–25°. The mixture is quenched with phosphate buffer (pH=7, 10 ml) and then filtered to remove the insoluble mercury salts. The phases are separated and the aqueous layer is back-extracted with methylene chloride (3 times). The organic phases are combined and washed with saline, dried over sodium sulfate and concentrated under reduced pressure to give the title compound. NMR (CDCl$_3$) 0.70, 1.42, 2.33, 5.60 and 5.80δ.

EXAMPLE 5

17β-Ethynyl-17α-hydroxyandrost-4-en-3-one (IIA)

3β-Methoxyandrosta-3,5-dien-17-one (IAa, 20 g), milled potassium hydroxide (16.5 g), t-butanol (2.5 g) and THF (75 ml) are placed in an inerted pressurizable vessel. While maintaining a nitrogen purge the vessel is cooled to −15°. The vessel is sealed and a 15 lb partial pressure of acetylene is applied. These conditions are maintained for 3 hrs after which TLC indicates complete conversion to ethisterone enol ether (17α-ethynyl-17β-hydroxy stereochemistry). Ethylene diamine (13 ml) is then added. The mixture is heated to 55°–65° for 1 hr maintaining 20 lb/in$^2$ pressure. TLC indicates the title compound. Water is added and the solvent by vacuum to give a solid which is recrystallized from isopropanol to give the title compound.

CHART A

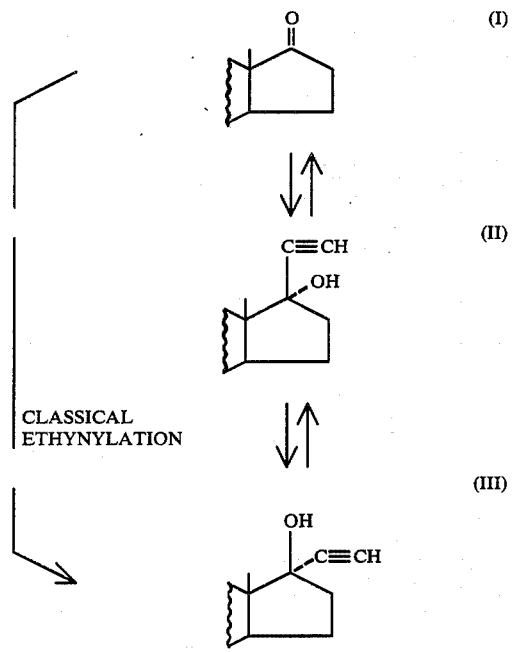

CHART B

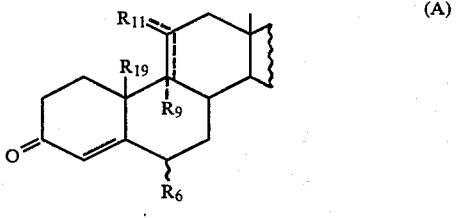

-continued
CHART B (B)
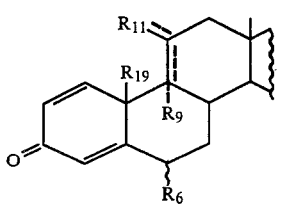

(C)
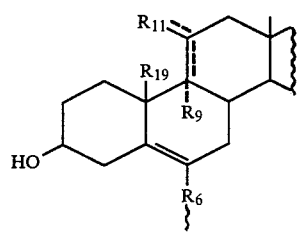

CHART C (Aa)
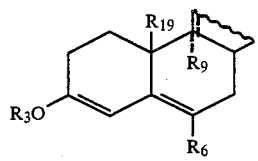

(Ab)
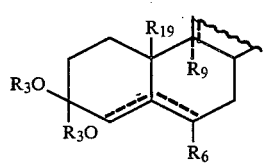

(Ac)
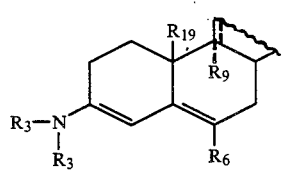

(Ca)
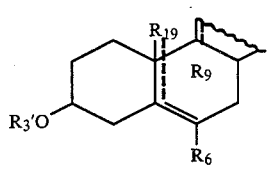

I claim:
1. A process for the preparation of a 17β-ethynyl-17α-hydroxy steroid of the formula

(II)
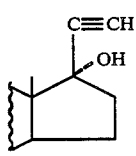

in greater than 25% chemical yield which comprises
(1) contacting a 17-keto steroid of the formula (I)
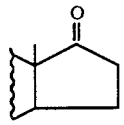

with an acetylene source in the presence of a strong base with an epi-amine solvent selected from the group consisting of ethylenediamine, 1,3-propylenediamine, 1,2-diaminopropane, triethylenetetramine, 1,2-diaminocyclohexane, consisting at least 5% of the reaction medium;
(2) quenching the reaction mixture with a quenching agent.

2. A process according to claim 1 where the 17-keto steroid (I) is a $\Delta^4$-3-keto steroid of the formula (A)
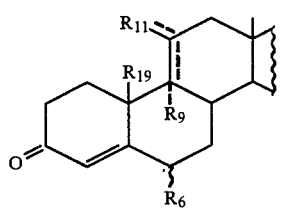

and the $C^3$ protected form is selected from the group consisting of
enol ether (Aa)
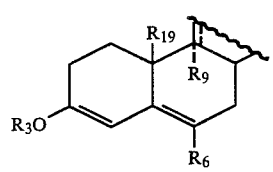

ketal (Ab)
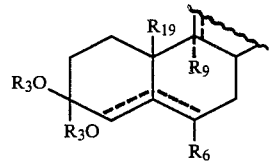

enamine (Ac)
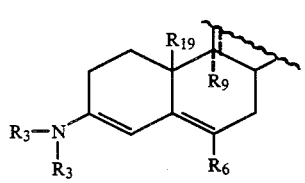

where $R_3$ is alkyl of 1 thru 5 carbon atoms with the proviso that with the ketal (Ab), and the enamine (Ac), the $R_3$ groups can be the same or different and can be connected;
$R_6$ is a hydrogen or fluorine atom or methyl or methylene group;

R$_9$ is nothing, a hydrogen, fluorine or oxygen atom which makes the C ring
(a) $\Delta^{9(11)}$ when R$_9$ is nothing and
(b) 9$\beta$,11$\beta$-epoxide when R$_9$ is an oxygen atom;

R$_{11}$ is a hydrogen or oxygen atom, two hydrogen atoms, or $\alpha$- or $\beta$-hydroxyl group which makes the C-ring
(a) $\Delta^{9(11)}$ when R$_{11}$ is a hydrogen atom,
(b) 9$\beta$,11$\beta$-epoxide when R$_{11}$ is an oxygen atom and .... between C$_{11}$ and R$_{11}$ is a single bond, and
(c) a ketone when R$_{11}$ is an oxygen atom and .... between C$_{11}$ and R$_{11}$ is a double bond;

R$_{19}$ is a hydrogen atom or methyl group;

$\sim$ indicates that the attached group can be in either the $\alpha$ or $\beta$ configuration; and .... is a single or double bond.

3. A process according to claim 1 where the 17-keto steroid (I) is a $\Delta^{1,4}$-3-keto steroid of the formula

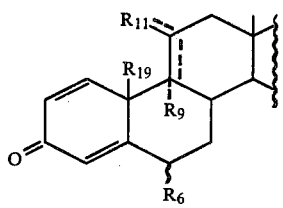
(B)

where R$_6$, R$_9$, R$_{11}$, R$_{19}$, $\sim$ and .... are defined in claim 2.

4. A process according to claim 1 where the 17-keto steroid (I) is a 3$\beta$-hydroxy-$\Delta^5$ steroid of the formula

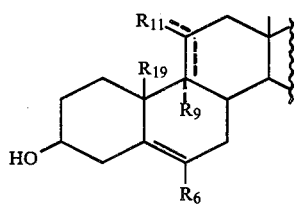
(C)

in its C$_3$ protected form
ether

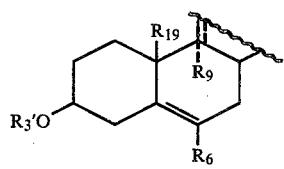
(Ca)

where R$_6$, R$_9$, R$_{11}$, R$_{19}$, $\sim$ and .... are defined in claim 2, and where R$_3'$ is alkyl of 1 thru 3 carbon atoms, a TMS, THP or EEE group.

5. A process according to claim 1 where the chemical yield is greater than 50%.

6. A process according to claim 1 where the acetylene source is selected from the group consisting of acetylene, calcium carbide, or potassium carbide.

7. A process according to claim 6 where the acetylene source is potassium carbide.

8. A process according to claim 1 where the strong base is of the formula OR$^-$ where R is alkyl of 1 thru 5 carbon atoms.

9. A process according to claim 1 where the strong base is selected from the group consisting of sodium or potassium, t-butoxide, i-propoxide, methoxide, ethoxide and hydroxide.

10. A process according to claim 9 where the strong base is potassium t-butoxide or hydroxide.

11. A process according to claim 1 where the epi-amine is selected from the group consisting of ethylenediamine, 1,3-propylenediamine, 1,2-diaminopropane and triethylenetetramine.

12. A process according to claim 11 where the epi-amine is ethylenediamine.

13. A process according to claim 1 where the reaction temperature is about 20° or greater.

14. A process according to claim 1 where the quenching agent is selected from the group consisting of acetic acid, water, aqueous buffer, saline.

15. A process for the preparation of a 17$\beta$-ethynyl-17$\alpha$-hydroxy steroid of the formula

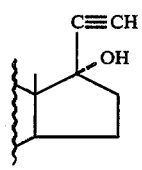
(II)

which comprises
(1) contacting a 17$\alpha$-ethynyl-17$\beta$-hydroxy steroid of the formula

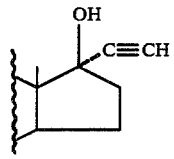
(III)

with a strong base in an epi-amine solvent selected from the group consisting of ethylenediamine, 1,3-propylenediamine, 1,2-diaminopropane, triethylenetetramine and 1,2-diaminocyclohexane constituting at least 5% of the reaction medium.

16. A process according to claim 15 where the 17-keto steroid (I) is a $\Delta^4$-3-keto steroid of the formula

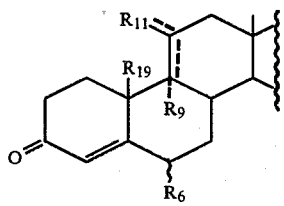
(A)

and the C$^3$ protected form is selected from the group consisting of
enol ether

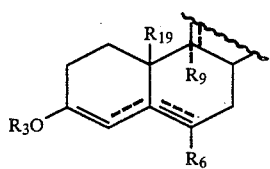

ketal

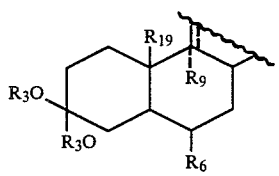

enamine

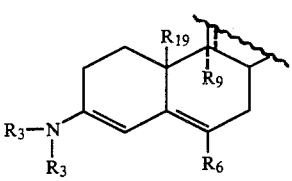

where $R_3$ is alkyl of 1 thru 5 carbon atoms with the proviso that with the ketal (Ab), and the enamine (Ac), the $R_3$ groups can be the same or different and can be connected;

$R_6$ is a hydrogen or fluorine atom or methyl or methylene group;

$R_9$ is nothing, a hydrogen, fluorine or oxygen atom which makes the C ring (a) $\Delta^{9(11)}$ when $R_9$ is nothing and (b) $9\beta,11\beta$-epoxide when $R_9$ is an oxygen atom;

$R_{11}$ is a hydrogen or oxygen atom, two hydrogen atoms, or $\alpha$- or $\beta$-hydroxyl group which makes the C-ring (a) $\Delta^{9(11)}$ when $R_{11}$ is a hydrogen atom, (b) $9\beta,11\beta$-epoxide when $R_{11}$ is an oxygen atom and .... between $C_{11}$ and $R_{11}$ is a single bond, and (c) a ketone when $R_{11}$ is an oxygen atom and .... between $C_{11}$ and $R_{11}$ is a double bond;

$R_{19}$ is a hydrogen atom or methyl group;

∼ indicates that the attached group can be in either the $\alpha$ or $\beta$ configuration; and .... is a single or double bond.

17. A process according to claim 15 where the 17-keto steroid (I) is a $\Delta^{1,4}$-3-keto steroid of the formula

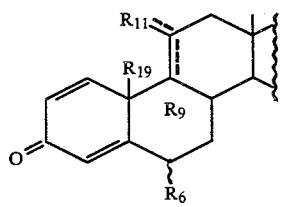

where $R_6$, $R_9$, $R_{11}$, $R_{19}$, ∼ and .... are defined in claim 16.

18. A process according to claim 15 where the chemical yield is greater than 50%.

19. A process according to claim 15 where the acetylene sourcce is selected from the group consisting of acetylene, calcium carbide, or potassium carbide.

20. A process according to claim 15 where the strong base is of the formula OR⁻ where R is alkyl of 1 thru 5 carbon atoms.

21. A process according to claim 15 where the strong base is selected from the group consisting of sodium or potassium, t-butoxide, i-propoxide, methoxide, ethoxide and hydroxide.

22. A process according to claim 15 where the epi-amine is selected from the group consisting of ethylenediamine, 1,3-propylenediamine, 1,2-diaminopropane and triethylenetetramine.

23. A process for the preparation of a 17β-ethynyl-17α-hydroxy steroid of the formula

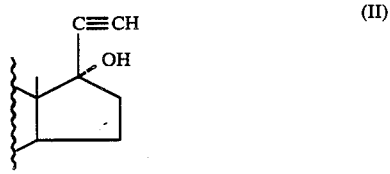

which comprises (1) contacting a 17-keto steroid of the formula

with an acetylene source in the presence of a strong base with an epi-amine solvent selected from the group consisting of ethylenediamine, 1,3-propylenediamine, 1,2-diaminopropane, triethylenetetramine, 1,2-diaminocyclohexane, constituting at least 5% of the reaction medium;

(2) quenching the reaction mixture with a quenching agent.

24. A process according to claim 23 where the 17-keto steroid (I) is a $\Delta^4$-3-keto steroid of the formula

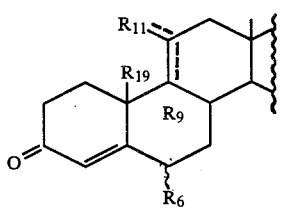

and the $C_3$ protected form is selected from the group consisting of
enol ether

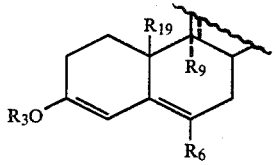

ketal

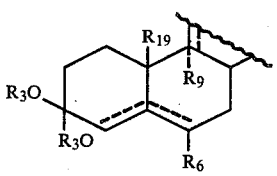

enamine

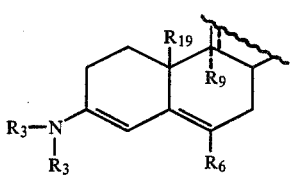

where $R_3$ is alkyl of 1 thru 5 carbon atoms with the proviso that with the ketal (Ab), and the enamine (Ac), the $R_3$ groups can be the same or different and can be connected;

$R_6$ is a hydrogen or fluorine atom or methyl or methylene group;

$R_9$ is nothing, a hydrogen, fluorine or oxygen atom which makes the C ring
(a) $\Delta^{9(11)}$ when $R_9$ is nothing and
(b) $9\beta,11\beta$-epoxide when $R_9$ is an oxygen atom;

$R_{11}$ is a hydrogen or oxygen atom, two hydrogen atoms, or $\alpha$- or $\beta$-hydroxyl group which makes the C-ring
(a) $\Delta^{9(11)}$ when $R_{11}$ is a hydrogen atom,
(b) $9\beta,11\beta$-epoxide when $R_{11}$ is an oxygen atom and .... between $C_{11}$ and $R_{11}$ is a single bond, and
(c) a ketone when $R_{11}$ is an oxygen atom and .... between $C_{11}$ and $R_{11}$ is a double bond;

$R_{19}$ is a hydrogen atom or methyl group;

~ indicates that the attached group can be in either the $\alpha$ or $\beta$ configuration; and
.... is a single or double bond.

25. A process according to claim 23 where the 17-keto steroid (I) is a $\Delta^{1,4}$-3-keto steroid of the formula

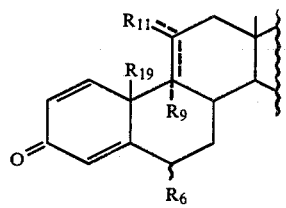

where $R_6$, $R_9$, $R_{11}$, $R_{19}$, ~ and .... are defined in claim 24.

26. A process according to claim 23 where the 17-keto steroid (I) is a $3\beta$-hydroxy-$\Delta^5$ steroid of the formula

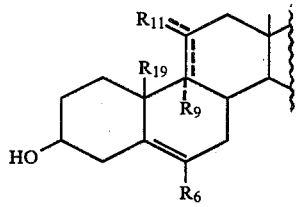

in its $C_3$ protected form
ether

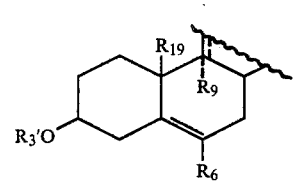

where $R_6$, $R_9$, $R_{11}$, $R_{19}$, ~ and .... are defined in claim 24 and where $R_3'$ is alkyl of 1 thru 3 carbon atoms, a TMS, THP or EEE group.

27. A process according to claim 23 where the acetylene source is selected from the group consisting of acetylene, calcium carbide, or potassium carbide.

28. A process according to claim 23 where the strong base is selected from the group consisting of sodium or potassium, t-butoxide, i-propoxide, methoxide, ethoxide and hydroxide.

* * * * *

UNITED STATES PATENT OFFICE

CERTIFICATE OF CORRECTION

Patent No. 4,582,644  Dated April 15, 1986

Inventor(s) Jean R. Runge

It is certified that error appears in the above-identified patent and that said Letters Patent are hereby corrected as shown below:

Column 1, line 7, "17α-hydroxy" should read --17β-hydroxy--
Column 4, line 67, "38%" should read --80%--
Column 5, line 32, "A, S. Pat.No." should read --A, US Pat.No.--
Column 6, line 24, "solvent by" should read --solvent removed by--
Column 7, line 50, " 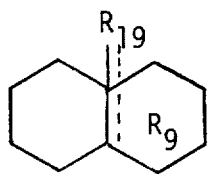 " should read -- 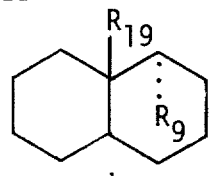 --

Column 8, line 13, "consisting" should read --constituting--
Column 11, line 5, " 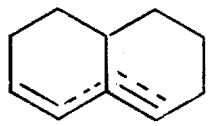 " should read -- 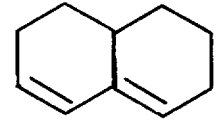 --

Column 11, line 16, " 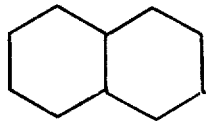 " should read -- 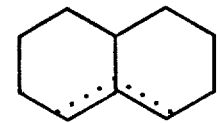 --

Column 11, line 61 " 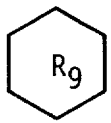 " should read -- 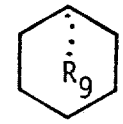 --

UNITED STATES PATENT OFFICE
CERTIFICATE OF CORRECTION

Patent No. 4,582,644                    Dated April 15, 1986

Inventor(s) Jean R. Runge

It is certified that error appears in the above-identified patent and that said Letters Patent are hereby corrected as shown below:

Column 12, line 5, "sourcce" should read --source--
Column 12, line 60, " 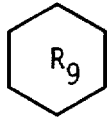 " should read -- 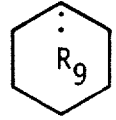 --

Signed and Sealed this

Eighteenth Day of November, 1986

*Attest:*

DONALD J. QUIGG

*Attesting Officer*   *Commissioner of Patents and Trademarks*